United States Patent [19]

Rao

[11] 4,379,780

[45] Apr. 12, 1983

[54] 17 α-DIHYDROEQUILIN HAPTEN AND ASSAY METHOD

[75] Inventor: Pemmaraju N. Rao, San Antonio, Tex.

[73] Assignee: American Home Products Corporation, New York, N.Y.

[21] Appl. No.: 191,807

[22] Filed: Sep. 29, 1980

[51] Int. Cl.³ .................... G01N 33/54; G01N 33/56; C07G 7/00; C07J 13/00
[52] U.S. Cl. ................................ 436/543; 260/397.4; 260/397.5; 260/112 B; 436/823; 436/817; 436/822; 436/804; 260/112 R
[58] Field of Search .............. 260/397.4, 397.5, 112 B; 424/1, 12; 23/230 B

[56] References Cited

U.S. PATENT DOCUMENTS 4,128,629 12/1978 Eldred et al. ........................ 424/1
4,293,536 10/1981 Jensen et al. ........................ 424/1

OTHER PUBLICATIONS

LaBella et al., Chem. Abstracts, vol. 90, 1979, Abstract #66958h.
Rance et al., J. Steroid Biochem., vol. 9, 1978, pp. 1065–1069.
Rao et al., Steroids, vol. 29, 1977, pp. 461–469.
Whittaker et al., Lancet, vol. 1, 1980, pp. 14–16.
Morgan et al., J. Steroid Biochem., vol. 13, 1980, pp. 551–555.
Johnson et al., J. Pharm. Sci., vol. 67, 1978, pp. 1218–1224.
Rao et al., Ligand Quarterly, vol. 3, No. 1, 1980, p. 53.

*Primary Examiner*—Christine M. Nucker
*Attorney, Agent, or Firm*—Arthur E. Wilfond

[57] ABSTRACT

A hapten is obtained by replacing the 3-hydroxy group of 17 α-dihydroequilin with HO—CO—A—O— wherein A is an alkylene of one to six carbon atoms. The hapten is conjugated with an immunological carrier to provide an immunogen, which in turn produces a specific antiserum to 17 α-dihydroequilin. The antiserum is used in a radioimmunoassay for 17 α-dihydroequilin.

10 Claims, No Drawings

17 α-DIHYDROEQUILIN HAPTEN AND ASSAY METHOD

RELATED APPLICATION

A related application is P. N. Rao, U.S. patent application Ser. No. 191,805, filed on the same day as this application.

BACKGROUND OF THE INVENTION

The present invention relates to a 17α-dihydroequilin hapten, to an immunogen for preparing an antiserum especially suited for use in the radioimmunoassay of 17α-dihydroequilin and to the antiserum. The invention also relates to a method of radioimmunoassay using the antiserum.

17α-Dihydroequilin, in the form of its 3-sulfate salt, is a major component of conjugated (equine) estrogens which are used for the treatment of menopausal disorders. The three major components of conjugated (equine) estrogens by weight are estrone sulfate (about 50%), equilin sulfate (about 25%) and 17α-dihydroequilin 3-sulfate (about 15%). Although 17α-dihydroequilin is known to be a potent estrogen, little is known about its pharmacologic action and metabolism. A tool, which would be extremely useful to acquire knowledge about these parameters, would be a specific antiserum for 17α-dihydroequilin.

Specific antisera have been developed for such estrogens as estrone, 17β-estradiol and estriol, for example, see P. N. Rao and P. H. Moore, Jr., Steroids, 29, 461 (1977). An antiserum also has been reported for equilin, see P. G. Whittaker et al., The Lancet, 1, 14 (1980) and M. R. A. Morgan et al., J. Steroid Biochem., 13, 551 (1980). This latter antiserum is derived from an immunogen obtained by attaching a steroid to an immunological carrier by means of an ester linkage, a form of attachment different from that of the present immunogen. Notwithstanding these developments, a specific antiserum for 17α-dihydroequilin had yet to be developed prior to the development of the antiserum of this invention.

Accordingly, the present invention fulfills the above-noted need by providing a specific antiserum for the radioimmunoassay of 17α-dihydroequilin. The antiserum has a minimum of cross reaction with other steroids found in serum and/or steroids which form the conjugates present in conjugated estrogens.

SUMMARY OF THE INVENTION

The hapten of this invention is represented by formula I

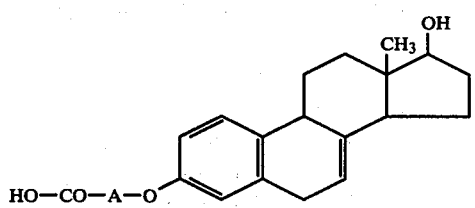

wherein A is an alkylene group of one to six carbon atoms.

The hapten can be used to prepare an immunogen and an antiserum. The antiserum is sufficiently specific to 17α-dihydroequilin in the presence of significant quantities of other steroids to enable a radioimmunoassay for 17α-dihydroequilin to be performed.

A preferred hapten is 1,3,5(10),7-estratetraene-3,17α-diol 3-O-carboxymethyl ether, i.e. the compound of formula I wherein A is methylene.

DETAILS OF THE INVENTION

The term "lower alkyl" as used herein means straight chain alkyl radicals containing from one to six carbon atoms and branched chain alkyl radicals containing from three to four carbon atoms, e.g. methyl, ethyl, propyl, 1-methylethyl, butyl, 1,1-dimethylethyl, pentyl and hexyl.

The term "alkylene" as used herein means a divalent organic radical derived from either a straight or branched chain aliphatic hydrocarbons, containing from one to six carbon atoms by removal of two hydrogen atoms, e.g. methylene, ethylene, 1-methylpropylene, 2-ethylpropylene and 2-butylethylene.

The terms "acyl" and "acylate" as used herein means straight chain 1-oxoalkyl radicals containing from one to ten carbon atoms and branched chain 1-oxoalkyl radicals containing from four to ten carbon atoms, e.g. formyl, acetyl, 1-oxopropyl, 1-oxobutyl, 2,2-dimethyl-1-oxopropyl, 1-oxohexyl and 1-oxo-3-ethyloctyl.

The term "lower alkoxy" as used herein means straight chain alkoxy radicals containing from one to six carbon atoms and branched chain alkoxy radicals containing three or four carbon atoms, e.g. methoxy, ethoxy, 1-methylethoxy, butoxy and hexanoxy.

The term "lower alkanol" as used herein means both straight and branched chain alkanols containing from one to four carbon atoms, e.g. methanol, ethanol, 1-methylethanol and butanol.

The term "halo" or "halogen" as used herein includes chlorine, bromine and iodine.

The term "organic proton acceptor" as used herein means the organic bases or amines, for instance, triethylamine, pyridine, N-ethylmorpholine and 1,5-diazabicyclo[4.3.0]non-5-ene.

The term "inorganic proton acceptor" as used herein means the inorganic bases, preferably the alkali metal hydroxides, carbonates and bicarbonates; e.g. sodium bicarbonate and potassium carbonate.

The term "proton acceptor" as used herein means a proton acceptor selected from an organic proton acceptor and an inorganic proton acceptor, as defined herein.

A convenient starting material to prepare the hapten of this invention is 17α-dihydroequilin, the preparation of which is described; for example, see D. J. Marshall, U.S. Pat. No. 3,507,889, issued Apr. 21, 1970.

17α-Dihydroequilin also is known as 1,3,5(10),7-estratetraene-3,17α-diol.

The hapten of formula I can be prepared by reacting 17α-dihydroequilin with an ester of the formula R$^1$O-CO—A—X in which R$^1$ is lower alkyl, A is as defined herein and X is halo in the presence of an organic or inorganic proton acceptor to obtain the corresponding lower alkyl ester of the compound of formula I. Hydrolysis of the latter compound under alkaline conditions gives the desired hapten of formula I in which A is as defined herein.

In a preferred embodiment, 17α-dihydroequilin is reacted with an excess, for instance five to ten molar equivalents, of a lower alkyl ester of a haloacetic acid, preferably ethyl bromoacetate, in the presence of sodium or potassium carbonate in an inert solvent, for example, dimethylformamide, ethanol or acetone. In this manner, 1,3,5(10),7-estratetraene-3,17α-diol 3-O-(lower alkoxy)carbonylmethyl ether is obtained. The latter compound is hydrolyzed with an alkali metal salt of a lower alkanol in a solution of the lower alkanol, preferably sodium ethoxide in ethanol, to give the described hapten of formula I in which A is methylene.

Alternatively, the hapten of this invention can be prepared by acylating 17α-dihydroequilin to obtain the corresponding 17α-dihydroequilin 3,17α-diacylate. Preferentially hydrolyzing the latter compound to obtain 17α-dihydroequilin 17-acylate. Reacting the 17α-dihydroequilin 17-acylate with an ester of the formula $R^1OCO—A—X$ in which $R^1$ is lower alkyl, A is as defined herein and X is halo in the presence of an organic or inorganic acceptor to obtain a compound of the formula

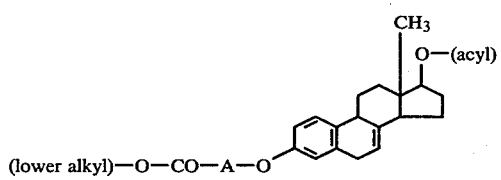

wherein A is as defined herein, and hydrolyzing the latter compound under alkaline conditions to obtain the hapten of formula I in which A is as defined herein.

In a preferred embodiment of the alternative procedure, 17α-dihydroequilin is reacted with acetic anhydride in the presence of an acid catalyst, for example, p-toluenesulfonic acid, sulfuric acid or perchloric acid, to obtain 1,3,5(10),7-estratetraene-3,17-diol 3,17α-diacetate. Preferential hydrolysis of the latter compound under mild alkaline condition, e.g. 1 to 5% (w/v) sodium or potassium carbonate in a lower alkanol, yields 1,3,5(10),7-estratetraene-3,17α-diol 17-acetate. Reaction of the latter compound with a lower alkyl ester of a haloacetic acid, preferably ethyl bromoacetate, in the presence of an inorganic proton acceptor gives 1,3,5(10),7-estratetraene-3,17α-diol 3-O-(lower alkoxy)-carbonyl ether 17-acetate. The latter compound then is hydrolyzed with an alkali metal salt of a lower alkanol in a solution of the lower alkanol, preferably sodium ethoxide in ethanol, to yield the hapten of formula I in which A is methylene.

The hapten of this invention is capable, when linked to a suitable immunological carrier, preferably a protein, to produce an immunogen which can be employed in a host animal to elicit anti-17α-dihydroequilin serum, specific to 17α-dihydroequilin. As used in this specification the term "immunogen" means a conjugate of a hapten and an immunological carrier, the immunogen being capable of causing an immunological response in a host animal. Among such carriers are proteins, polymers, polysaccharides and polypeptides, all of which should have a molecular weight of over 1000. The preferred carrier is bovine serum albumin (BSA); and other examples are the globulins, alpha-, beta-, gamma- and thyro-; and polylysine.

The conjugation of the instant hapten to the carrier can be done by procedures which are well known to those skilled in the art. Optionally, a coupling agent, for example a mixed anhydride, can be used.

The procedures for injecting the immunogen into a host animal and the recovery of the antibody are well known.

The antibody is employed in a radioimmunoassay for 17α-dihydroequilin. In accordance with such procedure, labeled steroid and unlabeled steroid present in a sample compete for binding sites on the antibody, and as a result of the competition, the ratio of bound labeled steroid to free labeled steroid diminishes as the concentration of unlabeled steroid in the sample increases. The amount of unlabeled steroid in a sample is obtained by comparing the inhibition observed with that produced by known amounts of unlabeled steroid, as presented in a standard curve. In this manner, a radioimmunoassay for detecting levels of 1,3,5(10),7-estratetraene-3,17α-diol (17α-dihydroequilin) in a sample is provided employing radiolabeled 1,3,5(10),7-estratetraene-3,17α-diol and an antibody for binding 1,3,5(10),7-estratetraene-3,17α-diol and radiolabeled 1,3,5(10),7-estratetraene-3,17α-diol. The assay is characterized by employing the specific antibody of this invention.

The 17α-dihydroequilin may be present in the sample, either as the free compound itself or conjugated in the form of its 3-sulfate salt. When an assay of the amount of 17α-dihydroequilin 3-sulfate present in a serum sample is required, the sample first is extracted with a water immiscible solvent to remove the unconjugated steroids. Thereafter the sample is subjected to mild acid hydrolysis to remove the sulfate portion and provide the 3-hydroxy steroid, i.e. 1,3,5(10),7-estratetraene-3,17α-diol. It should be noted that in this instance standard hydrolysis techniques cause a considerable amount of aromatization to occur in the substrate steroid where by the corresponding equilenin derivative is produced as a by-product. This transformation (aromatization) interferes with the assay of the steroid and, if not avoided, renders unreliable any assay method involving the conjugated form of equilin or an equilin derivative. A similar problem of the aromatization of equilin and 17α-dihydroequilin was reported in an earlier study by R. N. Johnson et al., J. Pharm. Sc., 67, 1218 (1978), and they did not find a satisfactory solution. This complication can be avoided by subjecting the sample of the conjugate to mild acid hydrolysis in the presence of a water soluble, non-protein binding antioxidant, for example, sulfur dioxide, chorobutanol or preferably ascorbic acid. An additional requirement is that the antioxidant does not interfere with the assay procedure. In practice, convenient and efficient hydrolysis conditions include mixing the sample with an equal volume of a solution of formic acid (10 to 50%, v/v), ascorbic acid (0.1 to 1%, w/v) in an inert solvent, for example, ethyl acetate or a lower alkanol. Normally the duration of the reaction will depend on the temperature employed. Convenient times and temperatures for the hydrolysis are from one to six hours and 20°–60° C., respectively.

The following examples further illustrate this invention.

EXAMPLE 1

1,3,5(10),7-Estratetraene-3,17α-diol
3-O-Ethoxycarbonylmethyl Ether

To a solution of 17α-dihydroequilin (1.0 g) in dry dimethylformamide (30 ml) was added anhydrous potassium carbonate (2.53 g) and the mixture was stirred under nitrogen for 15 min. Ethyl bromoacetate (2.4 ml) was added and the mixture was allowed to stir for 4 hr at 20° C. After that time, thin layer chromatography (TLC) in hexane:ethyl acetate (2:1, v,v) showed that the mixture no longer contained a detectable amount of 17α-dihydroequilin. The mixture was poured into ice water (300 ml) and extracted 3 times with diethyl ether (100 ml). The combined ether phases were washed successively with cold aqueous 1 N sodium hydroxide (100 ml), 0.1 N hydrochloric acid (100 ml) and water (100 ml). After evaporation of the solvent in vacuo, the title compound was obtained. The purity of the title compound (99.5%) was established by high pressure liquid chromatography (HPLC) on a 0.46×30 cm analytical Chromegabond Diol column (E. S. Industries, Marlton, N.J., U.S.A.). The column was developed using a concave gradient of 0.5 to 7% isopropanol in heptane over a period of 1 hr at a flow rate of 2 ml/min. The title compound had NMR (CDCl$_3$) δ 0.55 (s, 18-CH$_3$), 1.29 (t, J=7.5 Hz, —OCH$_2$CH$_3$), 3.10 (m, w$_{1/2}$=23 Hz, 9-H), 3.40 (m, w$_{1/2}$=11 Hz, 6Hs), 3.83 (d, J=6 Hz, 17β-H), 4.28 (q, J=7.5 Hz, —OCH$_2$CH$_3$), 4.60 (s, —OCH$_2$CO$_2$Et), 5.43 (br.s, 7-H), 6.67 (s, 4-H), 6.73 (d of d, J=8, 3 Hz, 2-H), 7.17 (d, J=8 Hz, 1-H)ppm.

EXAMPLE 2

1,3,5(10),7-Estratetraene-3,17α-diol 3-O-Carboxymethyl Ether

The product from Example 1, (0.364 g) was dissolved in dry methanol (60 ml) and a solution of sodium methoxide (0.121 g) in methanol (9 ml) was added. The mixture was refluxed under nitrogen for 1 hr when TLC in hexane:ethyl acetate (2:1; v:v) showed that the hydrolysis was about 70% complete. After cooling, the solvent was removed in vacuo and the residue partitioned between 100 ml of diethyl ether and water. The pH of the aqueous phase was adjusted to pH 3 with 1 N hydrochloric acid and the precipitate extracted with ethyl acetate (100 ml). The ethyl acetate phase was washed with water (50 ml) and evaporated in vacuo, yielding 0.252 g of an oil. This oil was purified by dry column chromatography on silica gel using the solvent system diethyl ether:ethyl acetate:acetic acid (9:1:0.1; v:v:v). [The dry column chromatography for this example and examples 3 and 4, hereinafter, was performed on Woelm silica gel in a nylon column as described by B. Loev and M. M. Goodman, Prog. Separ. Purif., 3, 73 (1970).]. From this column 0.127 g of the title compound was obtained which was crystallized three times from acetone-hexane; m.p. 151°-153° C.; IR(KBr) 3460, 1735, 1610, 1580, 1500 cm$^{-1}$; NMR (CD$_3$OD) δ 0.57 (s, 18-CH$_3$), 3.10 (m, w$_{1/2}$=22 Hz9-H), 3.35 (m, w$_{1/2}$=11 Hz, 6-Hs), 3.78 (d, J=6 Hz, 17β-H), 4.60 (s, —OCH$_2$COOH), 5.45 (br.s, 7-H), 6.78 (s, 4-H), 6.75 (d of d, J=8.3 Hz, 2-H), 7.15 (d, J=8 Hz, 1-H)ppm; MS, m/e=328 (M+); λ$_{max}$(CH$_3$OH) 278 nm (ε=1,970), 286 (ε=1,750). Anal. Calcd for C$_{20}$H$_{24}$O$_4$: C, 73.15; H, 7.37 and Found: C, 73.02; H, 7.23.

EXAMPLE 3

Alternative Preparation of 1,3,5(10),7-Estratetraene-3,17α-diol 3-O-Carboxymethyl Ether 17α-Dihydroequilin (1 g), p-toluenesulfonic acid (1 g), and acetic anhydride (40 ml) were heated in an oil bath at 100° C. until a clear solution was obtained and then left at room temperature in the dark for 2 days. At this time TLC showed no detectable amount of 17α-dihydroequilin. The mixture was poured into a solution of pyridine (30 ml) and water (400 ml), acidified with 4 N hydrochloric acid and extracted with diethyl ether (300 ml). The ether phase was washed with water (150 ml) and evaporated to dryness in vacuo. The product was dissolved in methanol (75 ml), heated to 60° C. and water (40 ml) added. After cooling, 1.14 g of 1,3,5(10),7-estratetraene-3,17α-diol 3,17-diacetate was obtained, m.p. 124°-126° C.

The latter diacetate (1.14 g) was dissolved in 200 ml methanol-acetone (1:1, v:v), the solution cooled to 4° C., and a cold (4° C.) solution of potassium carbonate (0.5 g) in 95% methanol (200 ml) was added. After 35 min at 4° C. the solution was acidified with 1 N hydrochloric acid (7.2 ml). Most of the solvent was evaporated in vacuo and the residue was dissolved in diethyl ether (200 ml) and washed with water (100 ml). The ether phase was evaporated in vacuo. The product (1.0 g) failed to crystallize and was purified by dry column chromatography on silica gel using ethyl acetate:hexane (1:4, v:v), 1,3,5(10),7-Estratetraene-3,17α-diol 17-acetate was obtained as a colorless oil (0.784 g) after drying in high vacuum.

To a solution of the latter compound (0.784 g) in dry dimethylformamide (20 ml) was added anhydrous potassium carbonate (1.72 g) and the mixture stirred under nitrogen for 15 min. Ethyl bromoacetate (1.63 ml) was added and the mixture allowed to stir for 2.5 hr when TLC in hexane:ethyl acetate (2:1, v:v) showed the reaction was about 95% complete. The mixture was poured into ice water (200 ml) and extracted with diethyl ether (200 ml). The diethyl ether phase was extracted twice with 1 N hydrochloric acid (100 ml) and water (100 ml). After evaporation of the solvent, the product was purified by dry column chromatography on silica gel using ethyl acetate:hexane (1:4, v:v). 1,3,5(10),7-Estratetraene-3,17α-diol 3-O-ethoxycarbonyl ether was obtained as a colorless oil (0.926 g) after drying in high vacuum.

The latter compound (0.926 g) was dissolved in dry methanol (155 ml) and a solution of sodium methoxide (0.278 g) in methanol (20 ml) was added. The mixture was refluxed under nitrogen for 4 hr when TLC in hexane:ethyl acetate (2:1; v:v) showed that the hydrolysis was about 90% complete. After cooling, the solvent was removed in vacuo and the residue partitioned between 200 ml of diethyl ether and water. The aqueous phase was acidified to pH 3 with 1 N hydrochloric acid and the precipitate extracted with ethyl acetate graphy on silica gel using the solvent system diethyl ether:ethyl acetate:acetic acid (9:1:0.2; v:v:v). From this column 0.426 g of product was obtained which was crystallized three times from acetone-hexane; m.p. 153°-155° C.; MS m/e 328 (M+). Anal. Calcd for C$_{20}$H$_{24}$O$_4$: C, 73.15; H, 7.37 and Found: C, 73.14; H, 7.43. The product of this example was identical to the product of Example 2.

EXAMPLE 4

[2,4-$^3$H]-1,3,5(10),7-Estratetraene-3,17α-diol ([2,4-$^3$H]-labelled 17α-dihydroequilin)

For the radioimmunoassay, [2,4-$^3$H]-labeled 17α-dihydroequilin was prepared as follows:

17α-Dihydroequilin (0.120 g) was dissolved in methanol (35 ml), and concentrated ammonium hydroxide (35 ml) was added with stirring and the mixture cooled to 0° C. A solution of iodine (0.218 g in 15 ml methanol) was prepared and added dropwise to the mixture over a period of 30 min. After 1 hr of stirring at 0° C., glacial acetic acid (30 ml) was added and the mixture extracted twice with ethyl acetate (100 ml). The combined ethyl acetate phases were washed three times with water (50 ml) and dried in vacuo at 40° C. The residue was purified by dry column chromatography on silica gel using the solvent system hexane-ethyl acetate (4:1, v/v). The product (0.024 g) was crystallized from 50% aqueous ethanol to give pure 2,4-diodo-1,3,5(10),7-estratetraene-3,17α-diol; m.p. 108°–110° C. (dec); IR(KBr) 3425, 1450, 750 cm$^{-1}$; NMR(CDCl$_3$) δ 0.56 (s, 18-CH), 3.27 (m, w$_{1/2}$=9 Hz, 6-Hs), 3.80 (d, J=6 Hz, 17β-H), 5.43 (m, w$_{1/2}$=7 Hz, 7-H), 7.65 (s, 1 H)ppm; MS, m/e=552 (M+). Anal. Calcd for C$_{18}$H$_{20}$I$_2$O$_2$: C, 41.4; H, 3.85; I, 48.62 and Found: C, 41.28, H, 4.11, I, 48.61.

The tritiation of the latter compound was done by New England Nuclear Corporation, Boston, Mass., U.S.A. The 2,4-diiodo derivative (13 mg) was dissolved in ethyl acetate (5 ml). To this solution triethylamine (0.025 ml) and 5% Pd/Al$_2$O$_3$ catalyst (100 mg) were added and the reaction mixture stirred overnight at room temperature under an atmosphere of tritium gas. Labile tritium was removed in vacuo using methanol-methylene dichloride (1:1, v/v) as solvent. After filtration from the catalyst, the product was taken to dryness in vacuo to give a total of 1,328 mCi of [2,4-$^3$H]-1,3,5(10),7-estratetraene-3,17α-diol.

An aliquot from the above material (1 mCi) was dried under nitrogen and dissolved in 25 μl isopropanol. This was purified by HPLC, employing a 0.45×30 cm Chromegabond Diol column with a gradient of 3.75 to 15% isopropanol in heptane over a period of 40 min at flow rate of 3 ml/min. Fractions were collected at 0.5 min intervals and a 10 μl aliquot of each fraction was analyzed for its content of $^3$H radioactivity.

The $^3$H-labeled 17α-dihydroequilin was recovered as a single peak of radioactivity which was not completely separated from the radioactive peak of 17α-dihydroequilenin, which also was formed as a byproduct. The peak of radioactivity corresponding to 17α-dihydroequilin was combined, evaporated to dryness, and re-chromatographed as described above to obtain pure [2,4-$^3$H]-17α-dihydroequilin. The total radioactivity was found to be 236 μCi. From a standard curve of ultraviolet absorbance at 280 nm versus μg of unlabeled 17α-dihydroequilin injected on the column, the radioactive peak was determined to contain 3.40 μg of 17α-dihydroequilin. This yields a specific activity of 69.3 μCi/μg or 18.7 Ci/m mol for the purified compound.

EXAMPLE 5

Preparation of the steroid-bovine serum albumin conjugate and determination of the number of moles of steroid bound per mole of protein 1,3,5(10),7-Estratetraene-3,17α-diol 3-O-carboxymethyl ether (0.5 mmol) was coupled to bovine serum albumin (BSA, 583 mg) by a mild procedure developed by U. Axen, Prostaglandins, 5, 45 (1974) using N,N'-carbonyldiimidazole, as reported earlier, see P. N. Rao and H. P. Moore, Jr., Steroids, 28, 101 (1976). Ultraviolet spectral analysis, see B. F. Erlanger et al., J. Biol. Chem., 228, 713 (1957), and determination of the free amino groups in the conjugate by a quantitative ninhydrin procedure, see S. Moore and W. H. Stein, J. Biol. Chem., 211, 907 (1954), showed that the number of moles of steroid bound per mole of protein for the 17α-dihydroequilin-BSA conjugate by the two separate methods was 32 and 27, respectively.

EXAMPLE 6

Immunization Procedure; Collection of the Antibody and Assay Procedure

Five male New Zealand white rabbits, 4 months old, were used for immunization. The injection and bleeding schedules were exactly as reported previously by P. N. Rao and P. H. Moore, Jr., Steroids, 28, 101 (1976).

For the assay procedure, a standard was prepared from a stock solution of unlabeled steroid in absolute ethanol (100 ng/ml). A working standard solution containing 1 ng/ml of unlabeled steroid was prepared in sodium phosphate buffer (0.1 M, pH 7, 0.9% NaCl). The labeled [2,4-$^3$H]-17α-dihydroequilin solution was prepared in the assay buffer at a concentration of 100 pg/ml. The antiserum was prepared in BSA-assay buffer (1 g BSA/1000 ml sodium phosphate buffer) at a concentraton of one-fifth of the final working dilutions.

Plasma (0.2 ml) and distilled water (0.7 ml) were added to a 16×125 mm tube and mixed. [6,7-$^3$H]-Estrone-3-sulfate (0.1 ml, 2000 cpm, obtained from New England Nuclear Corp.), and [2,4-$^3$H]-17α-dihydroequilin (0.1 ml, 2000 cpm) was then added to correct for recovery through the assay procedure, and the sample again mixed well and allowed to stand at room temperature for 30 min. Diethyl ether (2 ml) was added for extraction of the free compound. The extraction was repeated three times and the combined extracts washed with distilled water (1 ml) and the solvent removed by evaporation. The aqueous phase containing the conjugates was re-extracted with 2 ml of ethyl acetate-ethanol (4:1, v/v). The extraction was repeated two more times and the combined extracts were dried in a centrifuge tube (12 ml) under a stream of nitrogen. Absolute ethanol was added to those tubes which contained residual water and once again dried under nitrogen. The conjugate fraction was hydrolyzed with formic acid. A solution of ethyl acetate (1 ml) containing formic acid (20%) and ascorbic acid (1 mg) was added to the tube containing the conjugate fraction. The tube was tightly closed, vortexed, and sonified for 10 min before being placed in a 37° C. water bath for 2 hr. The hydrolyzed sample was taken to dryness, sodium phosphate buffer (1 ml) was added, and the solution was vortexed and allowed to stand at 20° C. for 10 min. The hydrolyzed free compound was extracted with diethyl ether (2 ml) three times and taken to dryness. Assay buffer (0.4 ml) was added to the sample tube and mixed. Aliquots of 0.1 ml were removed to count for recovery and 0.1 ml (2×) were removed for assay.

The standard curve was established by preparing duplicate 3 ml centrifuge tubes containing 0, 50, 100, 250, 500, 1000, and 2000 pg of the steroid in a total volume of 0.5 ml assay buffer. The sample tubes were prepared in duplicate with hydrolyzed plasma extract (0.1 ml) and assay buffer (0.4 ml) in a total volume of 0.5 ml. To all standard and sample tubes antibody (0.25 ml) and labeled steroid (0.5 ml) were added. These were mixed and allowed to incubate at 4° C. for 18 hr. After addition of 0.2 ml gamma globulin dextran-coated charcoal (4 g charcoal, 0.4 g dextran, 0.8 g human gamma globulin, 200 ml deionized water), each tube was again mixed and placed in a cold room (4° C.) for 20 min. After centrifugation at 2,500 rev./min for 6 min, 0.5 ml of each supernatant was aliquoted into a counting vial. Then 15 ml of a scintillation medium [(4 g of 2,5-diphenyloxazole (PPO), 50 mg of 1,4-di-2-(5-phenyloxazoyl)benzene (dimethyl-POPOP), 100 ml of the aqueous solubilizer Biosolv BBS-3 (Biosolv is a trademark of Beachman Instruments, Irvine, Calif., U.S.A.) and 1000 ml toluene] was added to each vial. The samples were counted to a relative standard error of less than 2% in a Packard model 3320 liquid scintillation counter, Packard Instrument Co., Downers Grove, Ill., U.S.A., see C. Matthijssen and J. W. Goldzieher, Analyt. Biochem., 10, 401 (1965).

All rabbits immunized with the immunogen produced antisera with high titers and specificity in 6 months' time. The titer was determined from the ability of antibody to bind a constant amount (50 pg) of the labeled steroid. The cross-reactivity [(G. E. Abraham, J. Clin. Endorcrinol. Metabol., 29, 866 (1967)] of estrone with the anti-17α-dihydroequilin serum from each rabbit was determined. The antiserum with the lowest cross-reactivity and with sufficient titer and sensitivity was selected for further evaluation. The selected anti-17α-dihydroequilin serum had a titer of 1:125,000 at 50% binding with excellent specificity, having practically negligible cross-reaction with normal circulating estrogens or other estrogens of equine origin (Table 1). The binding affinity constant was determined by a Scatchard plot [G. Scatchard, Ann. N.Y. Acad. Sci., 51, 660 (1949)] was found to be $K_a = 7.7 \times 10^9$ l./mol. for the anti-17α-dihydroequilin serum.

TABLE 1

| Cross Reactivity Data | |
|---|---|
| Steroid | 17α-Dihydroequilin Antibody (Percent Cross-Reactivity) |
| Equilin | 0.7 |
| 17α-Dihydroequilin | 100.0 |
| Equilenin | 0.40 |
| 17β-Dihydroequilin | <0.10 |
| 8-Dehydroestrone | <0.10 |
| Estrone | <0.10 |
| 17α-Dihydroequilin 3-sulfate | 9.04 |
| 17α-Estradiol 3-sulfate | <0.10 |
| Equilin-7α,8α-glycol | <0.10 |
| 17α-Dihydroequilenin | <0.10 |
| 17β-Dihydroequilenin | <0.10 |
| Estradiol-17α | <0.10 |
| Estradiol-17β | <0.10 |
| 6-Dehydroestrone | <0.10 |
| 4-Androstene-3,17-dione | <0.10 |
| Androsterone | <0.10 |
| Dehydroepiandrosterone | <0.10 |
| Testosterone | <0.10 |
| Progesterone | <0.10 |
| Cortisol | <0.10 |

A study, using chromatography, showed that during hydrolysis of the conjugate fraction with formic acid approximately 13-16% of 17α-dihydroequilin was oxidized to 17α-dihydroequilenin respectively, as evidenced by high pressure liquid chromatography. In order to minimize this oxidation, 0.1% (w/v) ascorbic acid per sample was added to each sample before the hydrolysis with formic acid. By this procedure, the oxidation was minimized to 2-3%. In the actual assay procedure, no attempt was made to mathematically correct the final value due to the loss by oxidation. The overall recovery from plasma samples amounted to 72%.

In order to establish the usefulness of the antiserum in the actual radioimmunoassay, the following investigations have been performed:

(1) a known amount of 17α-dihydroquilin was added to pooled female plasma and the level of the 17α-dihydroequilin was determined by radioimmunoassay;

(2) increasing amounts of a standard mixture of free estrogens (Table 2), approximating the ratio of estrogens in conjugated estrogens, were added to plasma which already contained a known amount of 17α-dihydroequilin, and then the levels of total 17α-dihydroequilin were determined; and (3) known amounts of 17α-dihydroequilin 3-sulfate were added to plasma in the presence of increasing amounts of conjugated estrogens and then the levels of total 17α-dihydroequilin were determined after hydrolysis of the mixture of conjugates.

The results of these investigations are presented in Tables 3 through 5.

TABLE 2

Composition of a standard mixture of unconjugated estrogen present in conjugated estrogens as the 3-sulfates. Composition determined by gas liquid chromatography analysis

| STEROID | PERCENT |
|---|---|
| Estrone | 46.5 |
| Equilin | 25.6 |
| 17α-Dihydroequilin | 14.2 |
| 17α-Estradiol | 4.9 |
| Equilenin | 3.1 |
| 17α-Dihydroequilenin | 1.8 |
| 17β-Dihydroequilin | 1.72 |
| 8-Dehydroestrone | 1.51 |
| 17β-Dihydroequilenin | 0.42 |
| 17β-Estradiol | 0.26 |

TABLE 3

Recovery of 17α-dihydroequilin added to five 0.2 ml samples of pooled female plasma and measured in triplicate 17α-Dihydroequilin

| Estrogen added (ng) | Measured (ng)* | Recovery (1%) | Coefficient of variation (%) |
|---|---|---|---|
| 0 | n.d.+ | — | — |
| 0.25 | 0.252 | 101 | 7 |
| 0.50 | 0.511 | 102 | 6 |
| 1.00 | 0.967 | 97 | 6 |

*Corrected for recovery of internal standard of [2,4-$^3$H]-17α-dihydroequilin (average 74%).
+Not detectable.

TABLE 4

Recovery of 17α-dihydroequilin added as the reference standard, and/or in a standard mixture of unconjugated estrogens (Table 2), to five 0.2 ml samples of pooled female plasma and measured in duplicate

| 17α-Dihydroequilin added as reference standard (ng) | 17α-Dihydroequilin added in standard mixture (ng) | 17α-Dihydroequilin measured (ng)* | Difference (ng) | Coefficient of variation (%) |
|---|---|---|---|---|
| 0 | 0 | n.d.+ | — | — |
| 1.00 | 0 | 1.050 | 0.050 | 6 |
| 1.25 | 0 | 1.288 | 0.038 | 8 |
| 0 | 0.563 | 0.509 | −0.054 | 9 |
| 0.25 | 0.563 | 0.774 | −0.039 | 13 |
| 0 | 1.125 | 1.065 | −0.060 | 10 |
| 0.25 | 1.125 | 1.344 | −0.031 | 4 |

*Corrected for recovery of internal standard of [2,4-$^3$H]-17α-dihydroequilin (average 81%).
+Not detectable.

TABLE 5

Recovery of 17α-dihydroequilin from 17α-dihydroequilin 3-sulfate and conjugated estrogens added to five 0.2 ml samples of pooled female plasma and measured in duplicate

| ng 17α-Dihydroequilin added as the 3-sulfate | ng 17α-Dihydroequilin added in the conjugated estrogens* | ng 17α-Dihydroequilin measured** | Difference (ng) | Coefficient of variation (%) |
| --- | --- | --- | --- | --- |
| 0 | 0 | n.d.+ | — | — |
| 0.736 | 0 | 0.666 | −0.066 | 8 |
| 1.472 | 0 | 1.416 | −0.056 | 2 |
| 0 | 1.00 | 1.092 | 0.092 | 5 |
| 0.736 | 1.00 | 1.892 | 0.126 | 11 |
| 0 | 2.00 | 2.272 | 0.272 | 3 |
| 0.736 | 2.00 | 3.059 | 0.323 | 10 |

*Analyzed by gas liquid chromatography using the method of R. N. Johnson et al., cited above.
**Corrected for recovery of internal standard of [2,4-$^3$H]-estrone 3-sulfate (average 64%).
+Not detectable.

The recovery of 17α-dihydroequilin from plasma (after correction for the recovery of the $^3$H-labeled internal standard) was essentially quantitative within the 6 to 10% coefficient of variation of the procedure. A total recovery of 17α-dihydroequilin from the standard mixture of estrogens (Table 4), or after hydrolysis of their sulfate (Table 5), was also achieved within the variability of the method. From the data in Table 5, it would appear that there may be a 14% underestimation by g.l.c. of the amount of 17α-dihydroequilin in conjugated estrogens due to oxidation of this compound during hydrolysis in the absence of ascorbic acid.

In a study of plasma obtained from seven women 1 to 5 hours after they had received conjugated estrogens, namely the brand sold under the trademark "Premarin", per os (0.625 to 2.5 mg), the average ratio of total equilin to total 17α-dihydroequilin was 1.83 (range 1.04 to 2.64); the equilin being assayed by the method described in copending U.S. patent application No. AHP-7736, filed of even date of the present application, and the 17α-dihydroequilin being filed by the present method. The ratio of these components in the conjugated estrogens is also 1.83; see R. N. Johnson et al., J. Pharm. Sci., 67, 1218 (1978). Only about 6% of the total level of equilin in these samples of plasma was present as the free compound; i.e., extractable with diethyl ether prior to hydrolysis. Since the hydrolysis procedure employed does not act on estrone 3-glucosiduronate, it is reasonable to assume that 94% of the total level of equilin was present in plasma as equilin 3-sulfate. This is in agreement with the well established fact that estrone 3-sulfate is the major circulating endogenous estrogen in humans, R. H. Purdy et al., J. Biol. Chem., 236, 1043 (1961); H. J. Ruder et al., J. Clin. Invest., 51, 1020 (1972); and C. Longcope and K. I. H. Williams, J. Clin. Endorinol. Metabol., 38, 602 (1974).

I claim:

1. A compound of the formula

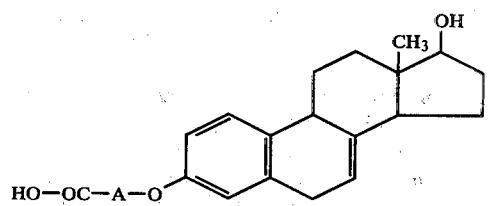

wherein A is an alkylene group of one to six carbon atoms.

2. 1,3,5(10), 7-Estratetraene-3,17α-diol 3-O-carboxymethyl ether as claimed in claim 1.

3. An immunogen comprising the compound of claim 1 conjugated to an immunological carrier.

4. An immunogen comprising 1,3,5(10),7-estratetraene-3,17α-diol 3O-carboxymethyl ether conjugated to an immunological carrier.

5. The immunogen of claim 4 wherein the carrier is bovine serum albumin.

6. The antibody produced by injecting the immunogen of claim 3 into a host animal.

7. The antibody produced by injecting the immunogen of claim 5 into a host animal.

8. In a radioimmunoassay procedure of 1,3,5(10),7-estratetraene-3,17α-diol in a sample employing radiolabeled 1,3,5(10),7-estratetraene-3,17α-diol and an antibody for binding 1,3,5(10),7-estratetraene-3,17α-diol and radiolabeled 1,3,5(10),7-estratetraene-3,17α-diol, the improvement which comprises employing the antibody of claim 6 or claim 7 in said radioimmunoassay procedure.

9. In a radioimmunoassay procedure of 1,3,5(10),7-estratetraene-3,17α-diol, wherein the sample for assay contains 1,3,5(10),7-estratetraene-3,17α-diol in the form of its 3-sulfate salt, the improvement which comprises subjecting the sample to hydrolysis conditions in the presence of a water soluble, non-protein binding antioxidant which does not interfere with the radioimmunoassay procedure.

10. In a radioimmunoassay procedure of 1,3,5(10),7-estratetraene-3,17α-diol, wherein the sample for assay contains 1,3,5(10),7-estratetraene-3,17α-diol in the form of its 3-sulfate salt, the improvement which comprises subjecting the sample to hydrolysis conditions in the presence of ascorbic acid.

* * * * *